United States Patent [19]

Vogel et al.

[11] Patent Number: 5,225,441
[45] Date of Patent: Jul. 6, 1993

[54] TREATMENT OF PERIODONTAL DISEASE

[75] Inventors: Richard I. Vogel, Riverdale; Kuo-Chen Yeh, Westfield, both of N.J.; Frank J. Sena, Brooklyn, N.Y.

[73] Assignee: Block Drug Company, Inc., Jersey City, N.J.

[21] Appl. No.: 63,324

[22] Filed: Jun. 18, 1987

[51] Int. Cl.$^5$ .................... A01N 37/00; A61K 31/19
[52] U.S. Cl. .................... 514/557; 514/560; 514/900; 514/901; 514/902
[58] Field of Search ......... 514/560, 557, 900, 901–902

[56] References Cited

U.S. PATENT DOCUMENTS

| 4,215,144 | 7/1980 | Thiele | 514/560 |
| 4,224,307 | 9/1980 | Thiele et al. | 514/560 |
| 4,513,008 | 4/1985 | Revici et al. | 514/560 |
| 4,752,618 | 6/1988 | Mascioli et al. | 514/560 |

FOREIGN PATENT DOCUMENTS 175468A  3/1986  European Pat. Off.
218460A  4/1987  European Pat. Off.

OTHER PUBLICATIONS

Terano, T., et al. Biochem. Pharmacol., vol. 35, No. 5, 1986, pp. 779–785.
Moncada, S., et al. Wiener Klinische Wochenschrift, vol. 98, No. 4, 1986, pp. 104–106.
Corey, E. J. et al. Proc. Natl. Acad. Sci., vol. 80, 1983, pp. 3581–3584.
Bang, Chemical Abstracts, 93(10):101482j (1980).
ElAttar, T. M. A., et al.: J. Dental Res., vol. 62, spec.issue 1983, p. 679, abstract.
ElAttar, T. M. A., et al.: J. Dental Res., vol. 62, No. 9, 1983, pp. 975–979.

Primary Examiner—José G. Dees
Assistant Examiner—Joseph M. Conrad
Attorney, Agent, or Firm—Ostrolenk, Faber, Gerb & Soffen

[57] ABSTRACT

Omega-3, 20-22 carbon atom, hexa- or penta-unsaturated fatty acids are used in the treatment of periodontal disease.

8 Claims, No Drawings

TREATMENT OF PERIODONTAL DISEASE

BACKGROUND OF THE INVENTION

Periodontal disease is an inflammatory disorder of the supporting tissue of the teeth. In the absence of control, the chronic inflammatory process will destroy the hard and soft tissues which support the teeth and eventually result in the loss of those teeth.

At present, the treatment of periodontal diseases is one of the most difficult problems in dentistry and periodontal disease is the major cause of tooth loss in adults. Since the introduction of water fluoridation, as well as the widespread use of fluoride containing dentifrices by children in the United States, tooth loss due to tooth decay among children and adolescents has dramatically decreased. Unfortunately, the opportunity to become afflicted with periodontal disease has concomitantly increased.

The two most common periodontal diseases are chronic gingivitis which is inflammation of the gingiva, and chronic destructive periodontitis, which results from progressive resorption of the alveolar bone, increasing the mobility of the teeth and, in an advanced stage, tooth loss.

The prevention and treatment of periodontal disease has in the past primarily involved maintaining good oral hygiene, eliminating sub-gingival calcului, protruding fillings and soft tissue, as well as intraosseous pockets and occlusal traumas and establishing a periodontal environment which is easily kept clean by the patient. This treatment is, unfortunately, not only protracted and expensive but also tends to require repetition throughout the individual's lifetime. It is frequently necessary to repeat periodontal surgery and even so, the long term effectiveness of the surgery has been limited.

Belgium Patent No. 900481 relates to a method of preventing or treating periodontal disease by using as the active agent either ibuprofen or flurbiprofen or a pharmaceutically acceptable lower alkyl salt or ester of these compounds administered orally, topically or buccally.

Thiele, in U.S. Pat. Nos. 4,097,604, 4,214,006 and 4,215,144 discloses a composition for the treatment of gingivitis and related periodontal diseases of the gingival tissue in which one of the components is a non-necrotic fatty acid compound which is prepared from an unsubstituted, unsaturated fatty acid having at least one double bond. These compounds are thought to be salts or esters and examples of the fatty acids used have 1, 2 or 3 double bonds. Included within the fatty acids set forth is 15-octadecenoic acid (trans form) $CH_3CH_2CH=CH(CH_2)_{13}COOH$.

Plaque has been determined to be the major etiologic factor in periodontal disease. It has been found that the inflammatory response induced by the plaque is responsible for most of the destruction associated with the disease.

Considerable evidence has implicated prostaglandin, particularly prostaglandin-$E_2$ ($PGE_2$), as components of the inflammatory reaction. Goodson et al., Prostaglandins, 6, 81-85 (1984) and El Attar et al., J. Periodontol, 52, 16-19 (1981) demonstrated that $PGE_2$ levels are elevated in inflamed gingiva when compared to normal gingiva. Offenbacher et al., J. Periodont. Res., 21, 101-112 (1986) demonstrated that extremely high levels of $PGE_2$ are present at periodontal sites of active attachment loss and low at sites which are in remission, i.e. there is no longitudinal attachment loss. The $PGE_2$ level in diseased tissue approximates 1 uM (Offenbacher et al. J. Periodon. Res. 19, 1-13 (1984)) which is a pharmacologically active concentration when tested in various model systems to induce vasodilation, bone resorption and other pro-inflammatory responses. Despite this evidence for the key role of $PGE_2$ in the pathogenesis of periodontal disease, relatively few studies have examined the use of drugs which inhibit $PGE_2$ synthesis in an attempt to retard or prevent periodontal tissue destruction.

It is the object of this invention to provide a new method and composition for the control and treatment of periodontal diseases. This and other object of the invention will become apparent to those of ordinary skill in this art from the following detailed description.

SUMMARY OF THE INVENTION

This invention relates to the treatment of periodontal disease and a composition therefor and more particularly to the use of an omega-3, 20-22 carbon atom, hexa- or penta- unsaturated fatty acid or salt thereof as the active agent in the fight against periodontal disease.

DETAILED DESCRIPTION OF THE INVENTION

As a result of epidemiological studies which were conducted during the 1970's, an unusual low incidence of cardiovascular disease was noted among those Greenland Eskimos who followed a traditional way of life. It was concluded that this was the result of the Eskimos' abundant consumption of seafood which is rich in n-3 polyunsaturated fatty acid (omega-3 PUFA) and their lower ingestion of n-6 polyunsaturated fatty acids (omega-6 PUFA). The two most common omega-3 PUFA are eicosapentaenoic acid (hereinafter "EPA")

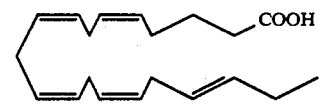

and docosahexaenoic acid (hereinafter "DHA"),

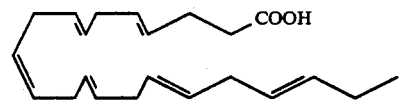

The two most common omega-6 PUFA are arachidonic acid

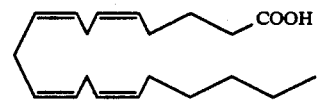

an linoleic acid.

Most arachidonic acid is formed from dietary linoleic acid by sequential desaturation and elongation, although arachidonic acid can also be obtained in the diet. When acted upon by cyclooxygenase, endoperoxides oxides such as $PGG_2$ and $PGH_2$ are formed and these, in turn, yield the biologically active prostaglandins such as $PGE_2$, $PGF_2$ and the like.

It was recognized that the omega-3 PUFA can compete with the omega-6 PUFA as a substrate in the arachidonic acid cascade and can therefore alter the synthesis of prostaglandin (from the cyclooxygenase pathway) and leukotrienes (from the lipoxygenase pathway), both of which are powerful mediators of inflammation and immune response. If either the cyclooxygenase or the lipoxygenase pathways, or both, are decreased by these agents, plaque-induced gingival inflammation and the destruction which is associated therewith can be decreased. Thus, if the omega-3 PUFA inhibits PGE synthesis in the gingival tissue, they can very well have therapeutic value in the treatment of both gingivitis and periodontitis when administered either systemically or applied topically. Accordingly, the following in vitro testing was effected.

Inflamed human gingival tissue was obtained from patients with periodontitis who were undergoing routine periodontal surgery. The tissues were immediately stored in liquid nitrogen prior to use or were used fresh. The assay of cyclooxygenase products was performed as a modification of the assay of El Attar et al., J. Periodon. Res., 21, 169-176 (1986). Pooled tissue was weighed and homogenized at 0°-4° C. with a polytron (Brinkman) homogenizer in a 0.2 M TRIS buffer, pH 8.0, at a final concentration of 20 mg/ml. After centrifugation for 10 minutes at 1200×g, the supernatant was divided into 3 ml aliquots for incubation in the presence or absence of a test compound. The test compounds were tested in triplicate over a log range of $10^{-3}$ to $10^{-9}$ M. The reaction was started by the addition of 0.2 uCi of $^{14}C$ arachidonic acid and carried out for 2 hours at 37° C. The reaction was stopped by the addition of two volumes of ethanol and allowed to remain at room temperature for 30 minutes prior to centrifugation for 10 minutes in order to remove the precipitate. The prostaglandin was then extracted.

Prostanoids were extracted as described by Powell, Methods in Eng., 86, 467 (1982) using a Sep-Pak-$C_{18}$ cartridge from Walters Associates. The Sep-Pak was prepared by the sequential elusion of 20 milliliters of ethanol and 20 milliliters of water. The sample was then adjusted to 15% ethanol, pH 3.0, with acetic acid and applied to the column. The column was eluted with 20 ml of 15% ethanol, pH 3.0, 20 ml of petroleum ether and then the prostaglandin and Tx (thromboxane) was eluded with 10 ml of methyl formate. Thereafter, the methyl formate was evaporated to dryness with nitrogen and reconstituted in 32% acrylonitrile (high-pressure liquid chromatography buffer).

Previous experience had revealed that the recovery was greater than 92% from $PGE_2$, $PGI_2$ (as 6KFl), $TxA_2$ (as $TxB_2$) and $PGF_2$. These are readily separated and quantified using a 4.6×100 mm RP-18 Spheri-5u column from Brownlee Labs. A Flow-One radioactivity monitor simultaneously measured radioactivity. The elution was monitored at 192 nanometers.

The net incorporation of the $^{14}C$ arachidonate was measured in the absence of the test substance in order to determine the maximal activity of the cyclooxygenase cascade. The percent inhibition for the inhibitors tested was then determined at several concentrations in order to calculate the $IC_{50}$. The results were as follows:

| Drug Concentration (M) | % Control |
|---|---|
| Effect of docosahexaenoic acid on periodontal cyclooxygenase: | |
| 0 | 100.0 |
| $5 \times 10^{-8}$ | 67.1 |
| $5 \times 10^{-7}$ | 59.3 |
| $5 \times 10^{-6}$ | 53.7 |
| $1 \times 10^{-4}$ | 38.8 |
| Calculated $IC_{50}$ = 1.0 × $10^{-5}$M | |
| Effect of eicosapentaenoic acid on periodontal cyclooxygenase: | |
| 0 | 100.0 |
| $5 \times 10^{-7}$ | 92.9 |
| $5 \times 10^{-6}$ | 60.1 |
| $1 \times 10^{-5}$ | 54.1 |
| $1 \times 10^{-4}$ | 30.6 |
| Calculated $IC_{50}$ = 1.5 × $10^{-5}$M | |
| Effect of ibuprofen on periodontal cyclooxygenase: | |
| 0 | 100.0 |
| $10^{-6}$ | 92.6 |
| $10^{-5}$ | 55.6 |
| $10^{-4}$ | 27.5 |
| Calculated $IC_{50}$ = 1.5 × $10^{-5}$M | |

The ibuprofen, a non-steroidal anti-inflammatory drug, was included in the testing because it had been found to be effective in the inhibition of periodontally supporting bone loss (which is the clinical index of periodontal disease progression) in a beagle dog model as shown in the aforementioned Belgian patent. As can be seen from the results set forth above, the eicosapentaenoic acid has the same calculated $IC_{50}$ as ibuprofen and the docosahexaenoic acid is more active than ibuprofen in controlling periodontal cyclooxygenase.

In carrying out the method of the present invention, the omega-3 PUFA or a salt thereof such as the sodium or potassium salts can be administered orally, topically or buccally to the patient being treated. Suitable forms of oral administrated are tablets, capsules, pills, powder, granules, solutions, suspensions and the like. Sterile aqueous solutions or suspensions can be advantageous for injection and advantageous topical forms of administration include gels, paste or an adhesive covering containing the agents. Suitable formulations for buccal administration are slow-dissolving tablets, pastilles, chewing gums, gels, a paste or a powder, for instance adapted to be applied to the gums, including toothpaste and dental adhesives, mouthwashes and chewing gums.

The compositions which are provided in accordance with the present invention include an effective periodontal disease reducing amount of the omega-3 PUFA in combination with a pharmaceutically acceptable carrier therefor. The carriers include such materials as lubricants, e.g. stearic acid or magnesium stearate, fillers such as lactose, sucrose and corn starch, desegregating agents such as algeic acid, surface active agents for use in injectable solutions or suspensions, and the like. The individual pharmaceutically acceptable carriers and the method used to form the compositions including the active omega-3 PUFA are conventional and described in standard reference texts such as, for example, Remington's Pharmaceutical Sciences. The amount of the active agent in these compositions is typically about 0.1 to 50% by weight and preferably about 1 to about 20% by weight. The effective treatment amount varies depending on the particular omega-3 PUFA or salt, the particular type of formulation being employed, the mode of administration and the state of the periodontal disease being treated. As a general guideline, an amount from about 0.05 to 20 mg/kg and preferably from about 1 to 10 mg/kg per day can be employed.

Various changes and modifications can be made in the process and compositions of the present invention without departing from the spirit and scope thereof. The various embodiments which have been described herein were for the purpose of further illustrating the invention but were not intended to limit it.

What is claimed is:

1. A method for the treatment of periodontal disease which comprises bucally applying 0.05 to 20 mg/kg per day of an omega-3, 20-22 carbon atom, hexa- or penta-ethylenically unsaturated fatty acid or salt thereof to a host in need thereof.

2. The method of claim 1, wherein said fatty acid or salt thereof is eicosapentaenoic acid.

3. The method of claim 2, wherein the fatty acid or salt is administered in combination with a pharmaceutically acceptable topical carrier therefor.

4. The method of claim 1, wherein said fatty acid or salt thereof is docosahexaenoic acid.

5. The method of claim 4, wherein the fatty acid or salt is administered in combination with a pharmaceutically acceptable topical carrier therefor.

6. The method of claim 1, wherein the fatty acid or salt is administered in combination with a pharmaceutically acceptable topical carrier therefor.

7. The method of claim 1, wherein said amount is about 1 to 10 mg/kg per day.

8. The method of claim 1 wherein said omega-3 fatty acid or salt thereof is applied in the form of slow dissolving tablets, pastilles, chewing gums, gels, pastes, powders, dental adhesives or mouthwashes.

* * * * *